United States Patent
Paulsen et al.

(10) Patent No.: US 9,986,945 B2
(45) Date of Patent: Jun. 5, 2018

(54) DEVICES, SYSTEMS, AND METHODS FOR OBTAINING AND ANALYZING URINE FLOW RATE DATA USING ACOUSTICS AND SOFTWARE

(71) Applicant: Regents of the University of Minnesota, Minneapolis, MN (US)

(72) Inventors: Laura Paulsen, Cambridge, MA (US); Sean Elliott, Minneapolis, MN (US); Sean McAdams, Scottsdale, AZ (US); Fluvio Lobo Fenoglietto, Minneapolis, MN (US); Andrew Pisansky, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days. days.

(21) Appl. No.: 14/814,960

(22) Filed: Jul. 31, 2015

(65) Prior Publication Data
US 2016/0029942 A1 Feb. 4, 2016

Related U.S. Application Data

(60) Provisional application No. 62/031,279, filed on Jul. 31, 2014.

(51) Int. Cl.
| | | |
|---|---|---|
| *G01N 33/48* | (2006.01) |
| *A61B 5/20* | (2006.01) |
| *G06F 19/00* | (2018.01) |
| *A61B 5/00* | (2006.01) |
| *G01F 25/00* | (2006.01) |
| *G01F 1/66* | (2006.01) |
| *G01F 15/06* | (2006.01) |
| *G06G 7/58* | (2006.01) |

(52) U.S. Cl.
CPC ............ *A61B 5/208* (2013.01); *A61B 5/0004* (2013.01); *G01F 1/666* (2013.01); *G01F 15/066* (2013.01); *G01F 25/0038* (2013.01); *G06F 19/3487* (2013.01)

(58) Field of Classification Search
CPC .......... G06F 19/18; G06F 19/22; G06F 19/24; G01N 33/582
See application file for complete search history.

(56) References Cited

U.S. PATENT DOCUMENTS

| 4,314,484 A | 2/1982 | Bowman |
| 8,276,465 B2 | 10/2012 | Belotserkovsky |
| 8,567,258 B2 | 10/2013 | Belotserkovsky |
| 2009/0044637 A1 | 2/2009 | Paz |
| 2012/0227510 A1 | 9/2012 | Grumbles |

OTHER PUBLICATIONS

D. L. Hitt et al., "Urinary Flow Measurements Via Acoustic Signatures with Application to Telemedicine," American Institute of Aeronautics and Astronautics, Jun. 2009, 11 pages.
R. A. Santucci et al., "Male Urethral Stricture Disease," Journal of Urology, vol. 177, May 2007, pp. 1667-1674.
Newcastle Hospitals, *PeePod Wins National Aware for Newcastle Hospitals*, Jan. 5, 2014, 2 pages.
MMS (Medical Measurement Systems) *Flowtaker: Disposable Home Uroflowmeter*, © 2014, 2 pages.
Wikipedia, *Spectral Density*, May 11, 2017, 9 pages.

*Primary Examiner* — Eric S Dejong
(74) *Attorney, Agent, or Firm* — Patterson Thuente Pedersen, P.A.

(57) ABSTRACT

Flow rate measurement devices and systems for accurate urine analysis to determine benign prostatic hyperplasia (BPH) or urethral stricture disease (USD) generally comprise a recording unit, an analysis unit, and a transmission unit. The recording unit includes device hardware and/or software configured to record data related to urinary flow rate. The analysis unit includes device hardware and/or software configured to assess, analyze, evaluate, or otherwise appraise the recorded data. The transmission unit includes device hardware and/or software configured to transmit the recorded and analyzed data.

19 Claims, 9 Drawing Sheets

| Validation Trial (N) | Standard/Control Uroflow Method | | Embodiments | |
|---|---|---|---|---|
| | Max Flow Rate (ml/s) | Mean Flow Rate (ml/s) | Max Flow Rate (ml/s) | Mean Flow Rate (ml/s) |
| Avg. | 26 | 21.26666667 | 27.53844444 | 22.02916667 |
| SD | 1.697056275 | 1.078064109 | 1.621581745 | 1.215099548 |
| SE | 0.979795897 | 0.206709357 | 0.540527248 | 0.23983728 |

Max Flow T-Test    0.331650463
Mean Flow T-Test   0.440923834

DEVICES, SYSTEMS, AND METHODS FOR OBTAINING AND ANALYZING URINE FLOW RATE DATA USING ACOUSTICS AND SOFTWARE

RELATED APPLICATION

The present application claims the benefit of U.S. Provisional Application No. 62/031,279 filed Jul. 31, 2014, which is hereby incorporated herein by reference in its entirety.

TECHNICAL FIELD

Embodiments relate generally to obtaining and analyzing male or female urine data, and more particularly, to devices, systems, and methods for analyzing urine data for bladder outlet obstruction, urethral stricture disease, or other lower urinary tract symptoms using acoustics or visual data.

BACKGROUND

Bladder outlet obstruction is typically attributed to either benign prostatic hyperplasia (BPH) or urethral stricture disease. BPH is one of the most common diseases found in aging men. It is associated with lower urinary tract symptoms that affect the quality of life by interfering with daily activities and normal sleep patterns. Symptomatic (clinical) BPH is present in approximately 26% of men in the fifth decade of life, 33% of men in the sixth decade, 41% of men in the seventh decade, and 46% of men in the eighth decade of life and beyond.

Urethral stricture disease is a scarring of the urethra that is much less common, affecting less than 1% of the U.S. population, yet there are relatively few specialists in the country who surgically treat this disease. Surgeons who treat urethral stricture disease are typically based in large urban centers, meaning there could be a significant geographic distance separating patients from these specialists. Urethral strictures, or scar tissue, can lead to the narrowing and blockage of the urethra. Urethral stricture disease (USD) can affect up to 0.6% of the U.S. patient population, with more than 1.5 million office visits due to urethral strictures occurring between 1992 and 2000. In 2000, the U.S. economic burden associated with USD was nearly $200 M, excluding medication costs. Diagnosing USD increases health care expenditures by more than $6,000 per patient per year and patient personal expenditures for the disease are estimated between $16,000 and $17,000. Further, there are a limited number of urethral stricture surgeons and specialists across the U.S., so patients must frequently travel to a clinic for surgery and/or follow-up tests. Due to this inconvenience, approximately 24% of USD patients will miss work for additional hospital and/or clinic visits. Likewise, there is a less than 15% follow-up rate within 6 months of the procedure.

Traditionally, BPH and USD are diagnosed using standardized questionnaires about urinary symptoms, along with uroflowmetry data, which measures urinary flow rate per time. Uroflowmetry is commonly used in urology offices for diagnosis, as well as for follow up of patients that undergo surgical or medical intervention for urinary outlet obstruction. Standard uroflowmetry machines are relatively expensive and are typically available only in urology offices. Therefore, there is a need for cost-effective systems, devices, and methods that can be used by patients remotely, as well in urology offices, to provide accurate urine data for BPH and USD diagnosis.

SUMMARY

Embodiments of the present application substantially meet the aforementioned needs of the industry, being directed to devices, systems, and methods for obtaining and analyzing urine flow rate data using acoustics and software. In an embodiment, a urine flow rate measurement device comprises a memory and a processor configured to implement a recording unit including at least one sensor and configured to sense and record data related to urine flow rate; an analysis unit configured to analyze the recorded urine flow rate data; and a transmission unit configured to transmit the analyzed urine flow rate data to a remote device.

In another embodiment, a system for determining lower urinary tract symptoms, the system comprises a flow rate measurement device including a recording unit including at least one sensor and configured to sense and record data related to urine flow rate, and a transmission unit configured to transmit the urine flow rate data; and a remote device configured to receive the urine flow rate data and present a determination of lower urinary tract symptoms.

In another embodiment, a kit comprises a flow rate measurement device including a recording unit including at least one sensor and configured to sense and record data related to urine flow rate, and a transmission unit configured to transmit the urine flow rate data; a calibration device configured to calibrate the data related to urine flow rate sensed by the flow rate measurement device; and instructions for using at least one of the flow rate measurement device or the calibration device.

In another embodiment, a method of determining lower urinary tract symptoms comprises placing a flow rate measurement device proximate a urine receptacle, the flow rate measurement device configured to sense and record data related to urine flow rate; recording urine flow rate data with the flow rate measurement device; analyzing the recorded urine flow rate data; and presenting the analyzed urine flow rate data.

In a feature and advantage of embodiments, systems, devices, and methods can measure flow rates of urine being voided by a in an ambulatory, outpatient setting, such as at home or while traveling. Embodiments eliminate the need for the patient to schedule and attend an appointment with a physician to get his or her urine flow rate measured. In embodiments, the urine flow rate data measured can subsequently be transmitted to a healthcare provider, such as the patient's urologist, who may then be able to determine if the patient has normal flow or if a urethral stricture may be present and require a hospital or physician visit.

In another feature and advantage of embodiments, systems and devices utilize auditory information to determine the urinary flow rate of a patient. In embodiments, systems and devices utilize visual information to determine the urinary flow rate of a patient. In other embodiments, systems and devices utilize both auditory information and visual information to determine the urinary flow rate of a patient. In certain embodiments, systems and devices utilize auditory information to confirm, calibrate, or otherwise evaluate visual information. Likewise, in other embodiments, systems and devices utilize visual information to confirm, calibrate, or otherwise evaluate auditory information.

In another feature and advantage of embodiments, a simple data measurement device such as a microphone or video camera is utilized to record sound or wave amplitude and/or frequency of urination, thereby allowing for a portable, take-home device. In embodiments, patients can utilize a mobile, stand-alone, or hybrid mobile/stand-alone device to record and send the sound or video amplitude/frequency directly to their healthcare provider. In embodiments, the data transmission can be initiated by the patient. In other embodiments, the data transmission can be requested by the healthcare provider. As a result, patients can test their flow rate outside of a clinic. The ease of use of this device can also increase the likelihood that postoperative patients will perform follow-up tests, decreasing the chance that urethral strictures will go undiagnosed and untreated.

In another feature and advantage of embodiments, devices and systems are waterproof, thereby protecting the hardware components of the devices and systems.

In another feature and advantage of embodiments, devices and systems are disposable. In an embodiment, devices can be reused until dropped into liquid. For example, for elderly patients who may not have a smartphone, inexpensive and disposable stand-alone devices can be utilized.

The above summary is not intended to describe each illustrated embodiment or every implementation. The figures and the detailed description that follow more particularly exemplify these embodiments.

BRIEF DESCRIPTION OF THE DRAWINGS

Embodiments may be more completely understood in consideration of the following detailed description of various embodiments in connection with the accompanying drawings, in which.

While embodiments are amenable to various modifications and alternative forms, specifics thereof have been shown by way of example in the drawings and will be described in detail. It should be understood, however, that the intention is not to limit the disclosure or claims to the particular embodiments described. On the contrary, the intention is to cover all modifications, equivalents, and alternatives falling within the spirit and scope of the appended claims.

DETAILED DESCRIPTION OF THE DRAWINGS

Figure 1:
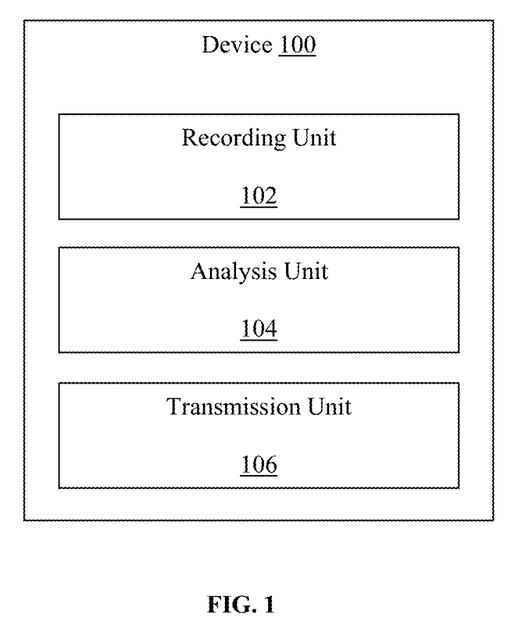
FIG. 1 is a block diagram of a flow rate measurement device, according to an embodiment.

Referring to FIG. 1, a block diagram of a flow rate measurement device 100 is depicted, according to an embodiment. Flow rate measurement device 100 generally comprises a recording unit 102, an analysis unit 104, and a transmission unit 106.

Recording unit 102 comprises device hardware and/or executable modules configured to record data related to urinary flow rate. According to embodiments, as will be discussed, recording unit 102 can comprise a stand-alone recording device. In other embodiments, as will be discussed, recording unit 102 can be integrated into a mobile device, such as a mobile phone, tablet, or personal digital assistant (PDA). In other embodiments, recording unit 102 can be a combination of a stand-alone device and a mobile device.

In an embodiment, recording unit 102 comprises an acoustic, vibration, or other audio sensor. For example, recording unit 102, in an embodiment, comprises a microphone configured to acquire auditory sounds created from urine striking an air-water interface, such as in a toilet, or some other air-material interface, such as in a urinal. In embodiments, recording unit 102 comprises a visual sensor, such as a camera. Recording unit 102 can further comprise a time-keeping module or device, such as a clock or oscillator, to allow for time-stamped data acquisition and sampling rate variation.

Analysis unit 104 comprises device hardware and/or executable modules configured to assess, analyze, evaluate, or otherwise appraise the recorded data. In embodiments, analysis unit 104 can output user-friendly results, such as in a graph, chart, list, or other readable format. Embodiments of analysis unit 104 are described further with respect to FIGS. 7 and 8A-8B.

Transmission unit 106 comprises device hardware and/or executable modules configured to transmit the recorded and analyzed data. Transmission unit 106 is configured for wired or wireless communication with outside devices. For example, transmission unit can comprise wireless hardware such as NFC hardware, RFID hardware, WIFI hardware, BLUETOOTH hardware, or any other suitable data transmission hardware and related circuitry, firmware, software, drivers, and other components. In such embodiments, transmission unit 106 comprises an antenna and drivers for the antenna. In another example, transmission unit 106 can comprise wired hardware and protocols such as USB, FIREWIRE, PS/2, EEPROM, ETHERNET, or any other suitable wired connection and appropriate connectors. In embodiments, transmission unit 106 can be integrated into recording unit 102.

As will be readily understood by one skilled in the art, any of recording unit 102, analysis unit 104, and/or transmission unit 106 can be implemented by suitable device hardware. For example, device 100 can comprise a processor/integrated circuit and memory.

A processor can be any suitable programmable device that accepts digital data as input, is configured to process the input according to instructions or algorithms, and provides results as outputs. In an embodiment, the processor can be a central processing unit (CPU) configured to carry out the instructions of a computer program. In other embodiments, the processor can be an Advanced RISC (Reduced Instruction Set Computing) Machine (ARM) processor or other embedded microprocessor. In other embodiments, the processor comprises a multi-processor cluster. The processor is therefore configured to perform at least basic selected arithmetical, logical, and input/output operations.

Figure 2:
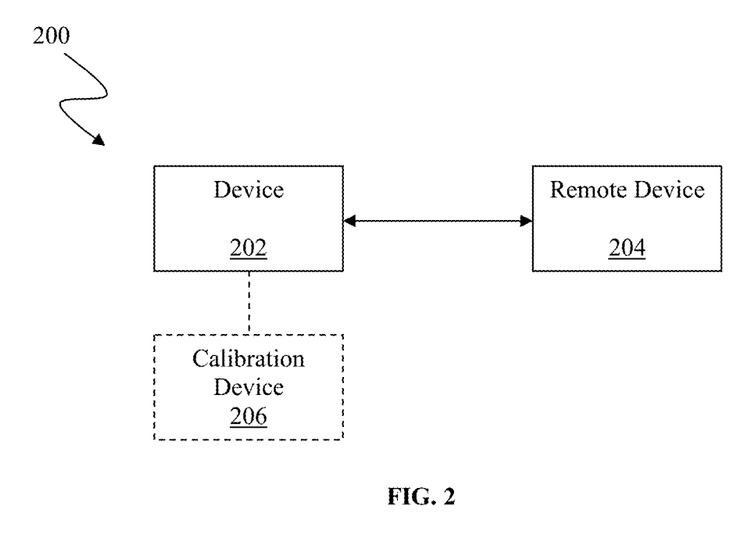
FIG. 2 is a block diagram of a flow rate measurement system, according to an embodiment.

Memory can comprise volatile or non-volatile memory as required by the coupled processor to not only provide space to execute the instructions or algorithms, but to provide the space to store the instructions themselves. The memory can further comprise space to store data collected by recording unit 102. In embodiments, volatile memory can include random access memory (RAM), dynamic random access memory (DRAM), or static random access memory (SRAM), for example. In embodiments, non-volatile memory can include read-only memory, flash memory, ferroelectric RAM, hard disk, floppy disk, magnetic tape, or optical disc storage, for example. The foregoing examples in no way limit the type of memory that can be used, as these embodiments are given only by way of example and are not intended to limit subject matter hereof. In other embodiments, the memory comprises a plurality of memory. For example, a first set of memory can be solely for use by the processor to store the instructions or algorithms, and a second set of memory can be solely for use in storing data collected by recording unit 102. Referring to FIG. 2, a block diagram of a system 200 utilizing a flow rate measurement device is depicted, according to an embodiment. System 200 generally comprises a flow rate measurement device 202 and a remote device 204.

In embodiments, flow rate measurement device 202 is substantially similar to flow rate measurement device 100. In other embodiments, as will be readily understood by one skilled in the art, components of flow rate measurement device 202 described with respect to device 100 can be integrated or comprised within remote device 204.

Remote device 204 is configured to be communicatively coupled with flow rate measurement device 202. In embodiments, remote device 204 comprises a smartphone, tablet, personal digital assistant (PDA), laptop computer, desktop computer, watch, wearable electronic device or other suitable remote device. As such, in embodiments, remote device 204 further comprises a processor, memory, and a graphical user interface (GUI). The processor of remote device 204 can be any suitable programmable device that accepts digital data as input, is configured to process the input according to instructions or algorithms, and provides results as outputs. Digital data, the instructions or algorithms, or other intermediary instructions or data can be stored in the memory of remote device 204. Outputs from the processor can be provided on the GUI.

In embodiments, flow rate measurement device 202 comprises a recording unit substantially similar to recording unit 102, and a transmission unit substantially similar to transmission unit 106. In such embodiments, remote device 204 comprises an analysis unit substantially similar to analysis unit 104 described with respect to device 100. However, as will be described, device 202 is configured for data recording and transmission, with remote device 204 configured for data analysis and presentation.

In embodiments, system 200 can optionally further comprise a calibration device 206. Calibration device 206 can comprise any suitable device or accessory configured to produce a known flow rate. For example, calibration device 206 can comprise a syringe attached to a motor, wherein a set volume can be loaded in the syringe and pumped by the motor to produce a constant, pre-set flow rate. In another example, calibration device 206 comprises a container having a pre-defined volume with connected tubing having pre-defined diameters. The user can fill the container to a pre-defined level, open a stopcock attached to the tubing, and then allow the liquid to flow from the container into the toilet until the level in the container reaches another pre-define level. This will generate a known flow rate based upon volume, tubing diameters, and properties of the liquid. In embodiments, the liquid is water.

Therefore, in embodiments, prior to or after data collection, a user can initiate a calibration test that allows the healthcare provider and data analyzer to obtain a point of reference for determining confidence in the accuracy of the analyzed data result. In embodiments, calibration device 206 generates a flow rate. The user can then turn on or activate flow rate measurement device 202 as if initiating a data collection trial, but instead use the calibration device 206 to produce a flow. The obtained flow can be compared to the pre-defined flow to generate a data collection accuracy confidence level.

As described initially with respect to device 100 and transmission unit 106, system 200 can further comprise a communication channel. The communication channel can operably couple any of flow rate measurement device 202, remote device 204, or calibration device 206. In embodiments of wireless communication, the communication channel generally comprises a wireless data channel, such as NFC, RFID, WIFI, or any other suitable channel. In embodiments of wired communication, the communication channel generally comprises wired hardware, such as USB, FIREWIRE, or PS/2 hardware on the respective components and channel.

In embodiments, system 200 can be packaged in a kit including a flow rate measurement device 202 and an optional calibration device 206. In another embodiment, the kit can further comprise a remote device 204. In embodiments, the kit can further include accessories such as mounting or fastening hardware for flow rate measurement device 202. In an embodiment, mounting or fastening hardware can comprise a suction cup. In other embodiments, mounting or fastening hardware can comprise a cantilevered arm or angled mechanical stop. In other embodiments, the kit can further include manufacturer instructions for use (IFU) or healthcare provider's orders for use.

Figure 3:
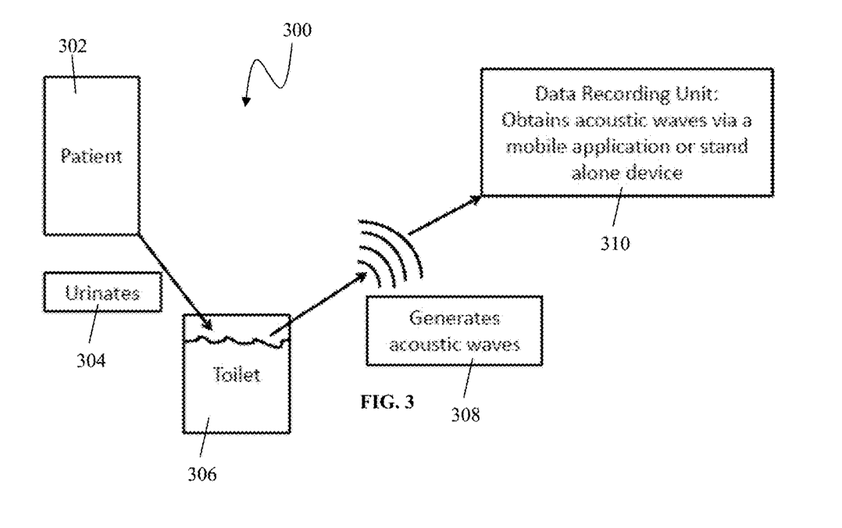
FIG. 3 is a block diagram flowchart of a flow rate measurement system, according to an embodiment.

Referring to FIG. 3, a block diagram flowchart of a flow rate measurement system 300 is depicted, according to an embodiment. System 300 can utilize or embody, for example, flow rate measurement device 100, flow rate measurement device 202, and/or system 200 as described with respect to FIGS. 1-2. As such, FIG. 3 generally depicts how flow rate measurement devices and systems are configured to utilize auditory information to determine the urinary flow rate of a patient.

System 300 comprises a patient 302 utilizing a flow rate measurement device as described above. At 304, patient 302 urinates into toilet 306. In other embodiments, as will be readily understood by one skilled in the art, toilet 306 can comprise a urinal or other appropriate voiding receptacle. At 308, acoustic waves are generated from the force of urination into toilet 306. At 310, the flow rate measurement device detects or senses the acoustic waves. For example, as described with respect to flow rate measurement device 100, recording unit 102 utilizes an audio sensor to detect, sense, measure, or otherwise monitor the acoustic waves.

Figure 4:
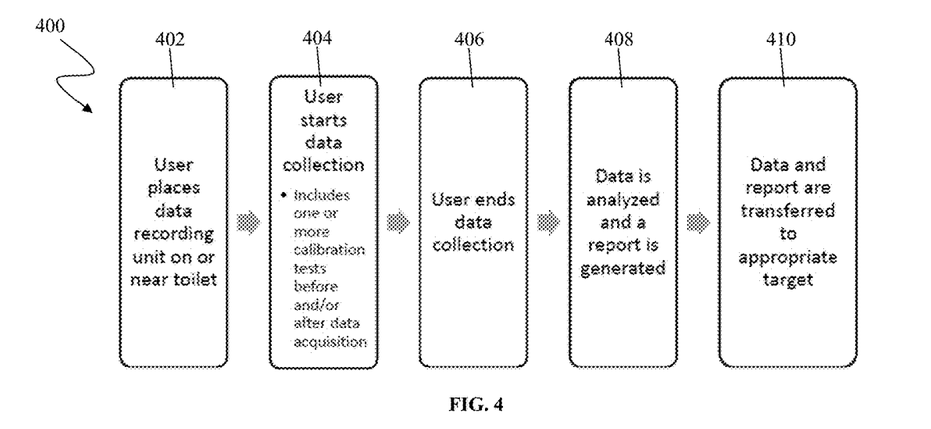
FIG. 4 is a flowchart of a method utilizing a flow rate measurement system, according to an embodiment.

Referring to FIG. 4, a flowchart of a method 400 utilizing a flow rate measurement system is depicted, according to an embodiment. Method 400 depicts the overall use of a flow rate measurement device in the context of a flow rate measurement system.

In general, method 400 can be initiated by at least two different initiation actions. In an embodiment, a patient can initiate a flow rate measurement test on his or her own. Data from the test can then be transferred to the patient's healthcare provider or hospital. In another embodiment, a patient's healthcare provider sends an alert to the patient. Such an alert can be a text message, email, phone call, or alert via the flow rate measurement device itself. The patient can then patient can initiate a flow rate measurement test. Data from the test can then be transferred to the patient's healthcare provider or hospital.

At 402, a user places a recording device on or near a toilet. In embodiments, the recording device can be a component of, for example, flow rate measurement device 100, such as recording device 102, or flow rate measurement device 202. In other embodiments, the flow rate measurement device can be placed proximate other receptacles. In embodiments, the flow rate measurement device is secured to a toilet or nearby fixture. In other embodiments, the flow rate measurement device is simply placed next to the toilet. In still other embodiments, the flow rate measurement device is held or worn by the user during use. In further embodiments, the flow rate measurement device is mounted or held by a stand, hanger, suction cup, temporary adhesive, or other holding device, which can optionally be included in the kit discussed above.

At 404, the user begins data collection with the flow rate measurement device. In an embodiment, the user can execute a calibration test prior to data collection. In another embodiment, the user can execute a calibration test after data collection. In other embodiments, a calibration test is conducted prior to data collection and also after data collection. Generally, at 404, the flow rate measurement device records urinary flow rate data. For example, recording device 102 can record urinary flow rate data.

At 406, data collection is ended. In an embodiment, data collection is terminated by the user interacting with the flow rate measurement device. For example, the user can interface with a graphical user interface to stop data collection. In other embodiments, data collection is terminated automatically by the flow rate measurement device, such as by a timer or by the lack of sound detected.

At 408, the data collected at 406 is analyzed. In embodiments, a report is generated. For example, analysis unit 104 can assess, analyze, evaluate, or otherwise appraise the data recorded as part of 404 and 406. In embodiments, referring to FIG. 1, the recorded data can be analyzed in, for example, device 100. In other embodiments, referring to FIG. 2, the recorded data can be analyzed in remote device 204. In other embodiments, portions of the recorded data can be analyzed in device 202, and portions of the recorded data can be analyzed in remote device 204.

At 410, the analyzed data can be output in the form of a report meeting the expectations and preferences of the healthcare provider, such as for automatic and/or convenient insertion into a patient electronic health record (EHR). In embodiments, the report or aggregated data can be transmitted to an appropriate remote device via wireless or wired communication. Data may be transmitted immediately after a data collection test or can be stored for an amount of time and then transmitted to a healthcare provider when requested or a certain time point is reached.

Figure 5:
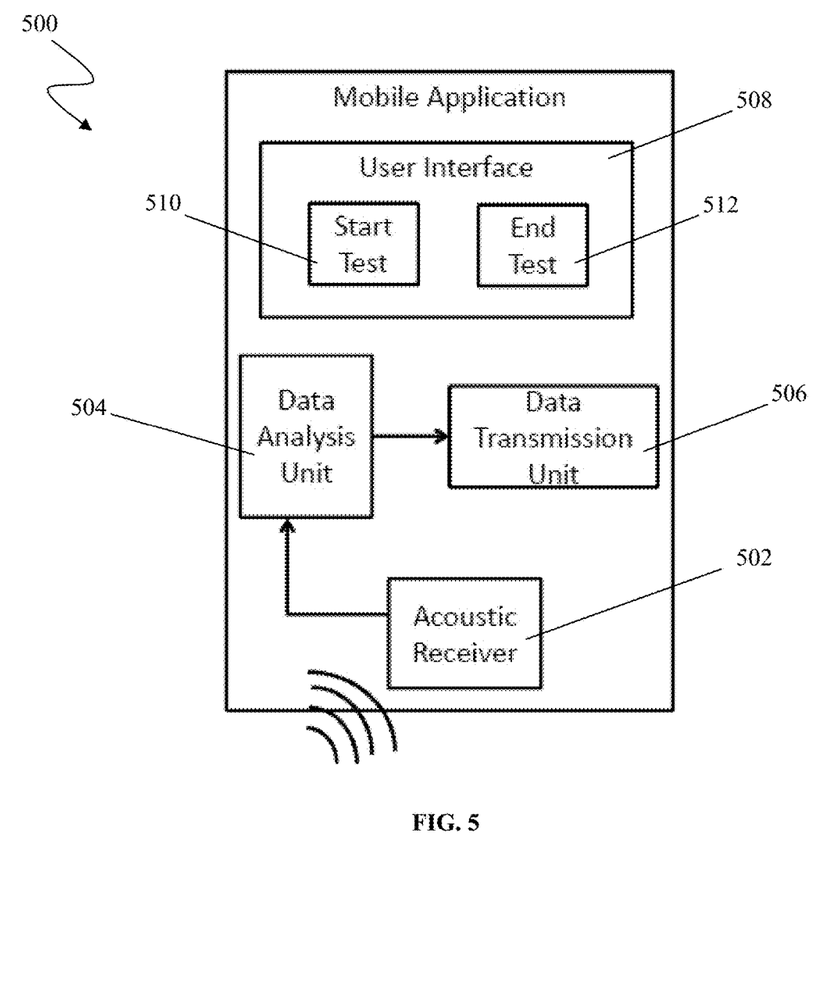
FIG. 5 is a block diagram of a remote device mobile application, according to an embodiment.

Referring to FIG. 5, a block diagram of a remote device mobile application 500 is depicted, according to an embodiment. In embodiments, remote device mobile application 500 can be integrated into an existing mobile device, such as a mobile phone, tablet, or PDA. As such, embodiments can leverage existing technology available in the electronic mobile unit (cell phone, tablet, etc.) including a sound receiver, processing unit, wireless or wired (such as through a USB connection) data transmission unit, and user interface. As depicted in FIG. 5, in one embodiment, mobile application 500 generally comprises an acoustic receiver 502, a data analysis unit 504, a data transmission unit 506, and a user interface 508.

Acoustic receiver 502 comprises mobile device hardware and/or executable modules configured to record data related to urinary flow rate. In embodiments, acoustic receiver 502 is substantially similar to recording unit 102.

Data analysis unit 504 comprises mobile device hardware and/or executable modules configured to assess, analyze, evaluate, or otherwise appraise the recorded data. In embodiments, data analysis unit 504 is substantially similar to analysis unit 104.

Data transmission unit 506 comprises mobile device hardware and/or executable modules configured to transmit the recorded and analyzed data. In embodiments, data transmission unit 506 is substantially similar to transmission unit 106.

User interface 508 is configured to display data recorded by acoustic receiver 502 or data analyzed by data analysis unit 504. In an embodiment, as depicted, user interface 508 comprises a graphical user interface having a Start Test button 510 and an End Test button 512. The user can interface to these buttons to either start or stop the flow test or flow data acquisition.

In operation of the mobile application 500 depicted in FIG. 5, a method of using mobile application 500 includes the patient performing two recordings. A first recording is used to filter the effect of the background/ambient noise and provide a calibration mechanism for analyzing the actual patient data. The first recording can be done before or after the second recording. A second recording comprises the flow data collection. This data, in combination with the calibration data of the first recording can then be analyzed and transmitted to the patient's healthcare provider.

Figure 6A:
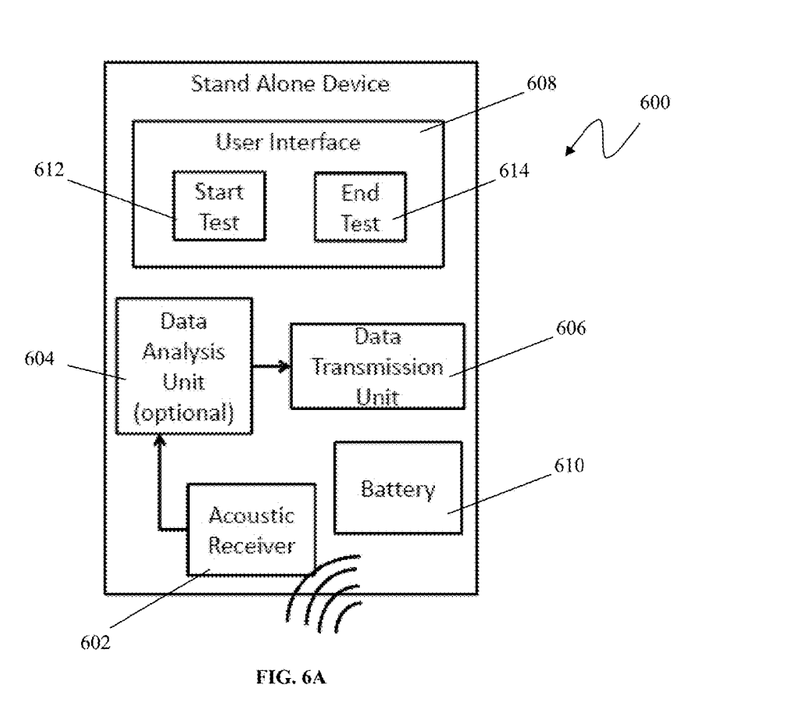
FIG. 6A is a block diagram of a stand-alone flow rate measurement device, according to an embodiment.

Referring to FIG. 6A, a block diagram of a stand-alone flow rate measurement device 600 is depicted, according to an embodiment. Device 600 can be substantially similar to mobile application 500, but can be configured to function independently. In an embodiment, as depicted in FIG. 6A, device 600 generally comprises an acoustic receiver 602, a data analysis unit 604, a data transmission unit 606, a user interface 608, and a battery 610.

Acoustic receiver 602 comprises device hardware and/or executable modules configured to record data related to urinary flow rate. In embodiments, acoustic receiver 602 is substantially similar to recording unit 102.

An optional data analysis unit 604 comprises device hardware and/or executable modules configured to assess, analyze, evaluate, or otherwise appraise the recorded data. In embodiments, data analysis unit 604 is substantially similar to analysis unit 104.

Data transmission unit 606 comprises device hardware and/or executable modules configured to transmit the recorded and analyzed data. In embodiments, data transmission unit 606 is substantially similar to transmission unit 106.

User interface 608 is configured to display data recorded by acoustic receiver 602 or data analyzed by data analysis unit 604. In an embodiment, as depicted, user interface 608 comprises a graphical user interface having a Start Test button 612 and an End Test button 614. The user can interface to these buttons to either start or stop the flow test or flow data acquisition.

Battery 610 is configured to provide power to one or more of the components of device 600, including acoustic receiver 602, data analysis unit 604, data transmission unit 606, or user interface 608. In an embodiment, battery 610 comprises a lithium-ion or other suitable battery. In embodiments, battery 610 is rechargeable.

Figure 6B:
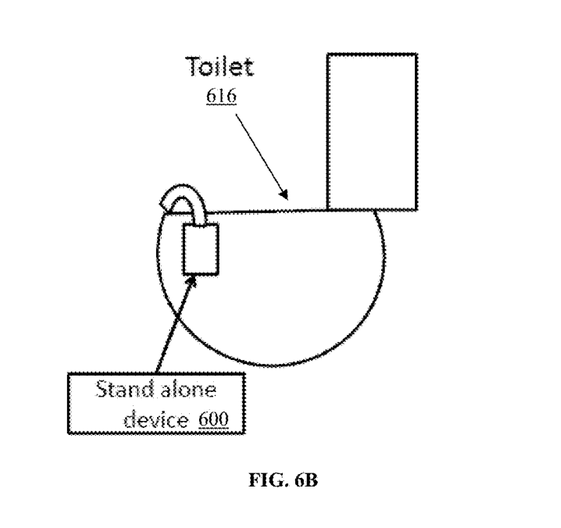
FIG. 6B is a block diagram of the stand-alone flow rate measurement device of FIG. 6A operably coupled to a toilet, according to an embodiment.

Referring to FIG. 6B, a block diagram of the stand-alone flow rate measurement device 600 of FIG. 6A operably coupled to a toilet 616 is depicted, according to an embodiment. As depicted, device 600 can be operably coupled to a dry region of toilet 616, such as on the lid, seat or lip, or can be positioned outside of toilet 616, but within an acceptable range of receiving the desired acoustic data. For example, device 600 can be placed on a floor, stand or shelf proximate toilet 616. In other embodiments, flow rate measurement device 600 can be operably coupled to a urinal or other appropriate voiding receptacle.

In operation of device 600 depicted in FIGS. 6A-6B, a method of using device 600 includes the patient performing two recordings similar to those recordings described above with respect to mobile application 500. Particularly, a first recording is used to filter the effect of the background noise and provide a calibration mechanism for analyzing the actual patient data. The first recording can be done before or after the second recording. A second recording comprises the flow data collection. This data, in combination with the calibration data of the first recording can then be analyzed and transmitted to the patient's healthcare provider. Further, device 600 can interface or operate in combination with a mobile application, such as mobile application 500 that analyzes the data (as will be described), but device 600 can also analyze the obtained data independently of other devices. Device 600 can then transmit the raw or analyzed data either wirelessly or through a wired connection.

In another embodiment, mobile application 500 and a device can be used in combination in a hybrid configuration. In such embodiments, a device can be substantially similar and externally visually the same as device 600, but internally comprise a data transmitter configured to access a wired or wireless communication channel between the device and mobile application 500. For example, in operation of a hybrid configuration, a patient can utilize the device for two recordings similar to those recordings described above with respect to mobile application 500 and device 600; a first recording for filtering background noise and calibrating the device and a second recording for data collection. Once recorded, the data from the device can be transmitted to mobile application 500 for analysis, presentation, or other post-recording use. The patient can activate the stand alone device and mobile application 500 simultaneously or sequentially.

In another embodiment (not depicted), a visual data receiver or recording device can be utilized in devices, systems, and methods. A visual data receiver is similar to the previously described auditory recording devices in method and ultimate goal, but is different in the data collected and analyzed. For example, instead of obtaining acoustic waves with a microphone, the visual data receiver can obtain measurements of physical waves generated from the patient's urine making contact with the liquid in the toilet bowl. For example, a visual data receiver can comprise a video camera configured to acquire the images of the physical waves created from urine striking an air-water interface, such as in a toilet.

In an embodiment, the visual data receiver can be a component of a stand-alone device such that the device is configured for both data acquisition and analysis. For example, the stand-alone device can function independently of a mobile application. The stand-alone recording device can be positioned in a dry region of the toilet, such as on the lid, seat or lip while still achieving sufficient visual contact of the waves to be created by the patient urinating. In embodiments, the visual-data based stand-alone device can be substantially similar to device 600 depicted in FIG. 6A, but comprise a visual data receiver instead of acoustic receiver 602. As such, the device can include a visual recording unit, microprocessor, data transmitter, user interface, and battery.

In another embodiment, the visual data receiver can itself be a discrete component that interfaces to a mobile application, such as mobile application 500 described with respect to FIG. 5. In embodiments, the mobile application can provide the user interface and data analysis portion of the system. The mobile application can obtain data from the visual-data based stand-alone device. The mobile application can analyze the data and ultimately transmit the data to another device or networked component, if desired. In still other embodiments, the visual data receiver can be a component of a mobile device.

Figure 7:
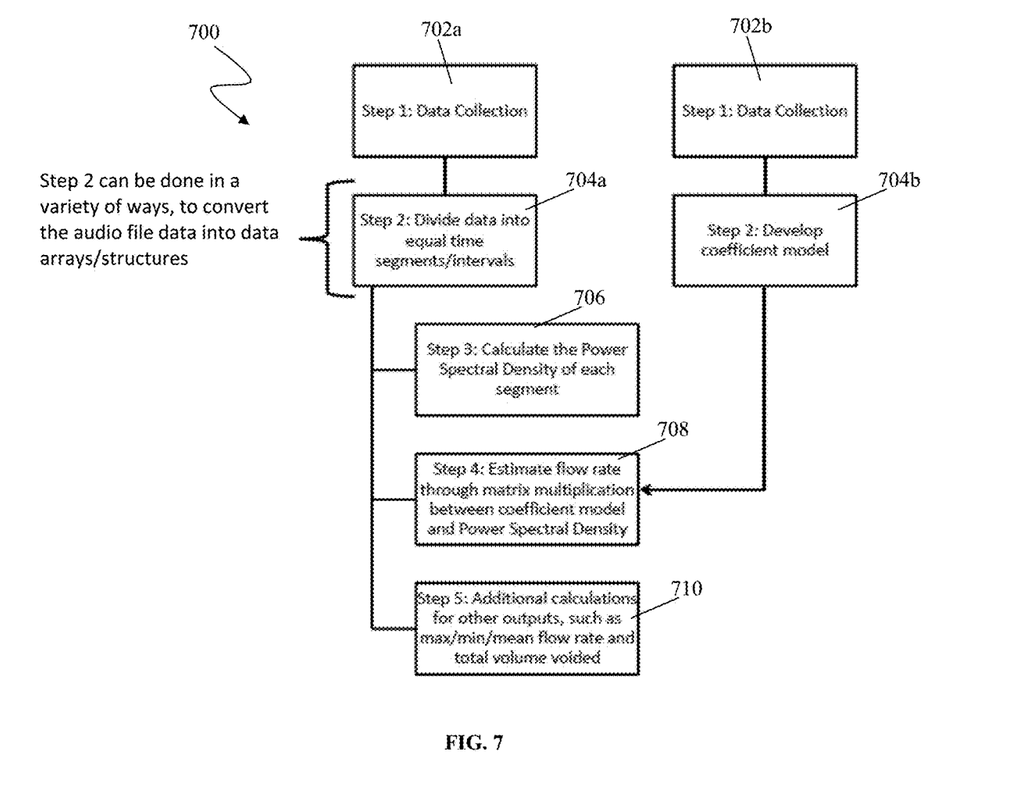
FIG. 7 is a flowchart of a method utilizing a flow rate measurement system, according to an embodiment.

Referring to FIG. 7, a flowchart of a method 700 utilizing a flow rate measurement device or system is depicted, according to an embodiment. In embodiments, method 700 comprises a data analysis method of flow rate data. Data collection and analysis of method 700 is intended to correlate a sound recording to a flow rate.

As depicted, method 700 comprises two paths initiated at data collection 702a and 702b. At 702a or 702b, data collection is conducted. In an embodiment, a device can obtain the uroflow data from the patient via the aforementioned visual and/or auditory methods. The data can be collected at various time points and can be initiated by the healthcare provider and/or user/patient. The device can allow a healthcare provider to initiate a test by alerting the patient via a communication method such as email or mobile text, or via the device itself. Embodiments of devices also allow a user to initiate a test. At 702a and 702b, data collection can comprise the same set of data collection.

In other embodiments, data collection 702b does not involve the patient. Instead, data collection 702b comprises bench top or engineering testing adapted to populate a matrix that can then be used to develop the coefficient model. In embodiment, the coefficient model (704b) is used to predict the flow rate from the patient's data collection (702a). In such embodiments, data collection, 702b and 704b are predetermined, with the resulting correlation coefficients embedded into modules for devices or mobile devices. In embodiments, different correlation coefficients for different devices or mobile devices are configured for varied patient requirements.

At 704a, along the first path of data collection from 702a, embodiments read or otherwise open or access the sound recording/signal for processing. Embodiments thereby allow for access to the signal's amplitude data, sampling rate, and time scale of the recording (recording duration). For example, an audio file may be in the form of a .wav or .mp3 file. Amplitude data can thereby be extracted from the audio file. In an embodiment, data can be divided into equal time segments or intervals and stored in a data structure, such as an array. Other data structure storage is also possible. Using the sound recording/signal (amplitude data), the signal's sampling rate, and its time-scale (recording duration), embodiments dissect/divide the signal into equal time segments/intervals for subsequent spectral analysis. In an embodiment, the length of the segments is determined based on the coefficient model, as discussed below with respect to 704b.

At 704b, a coefficient model is developed. In embodiments, coefficients are generated based on prior data collection and are independent from instant data collection, such as 702a. The coefficient model or coefficients can be generated in parallel to 704a and 706. In other embodiments, the coefficient model or coefficients can be generated prior to or after 704a and 706. In other embodiments, coefficients are generated and therefore exist prior to data collection 702a. In other embodiments, the data collection of 702b and coefficient model development at 704b are completed prior to data collection 702a. In embodiments, a coefficient matrix or coefficient model is not redefined on each run of the function/program, but rather embedded within the program itself.

In an embodiment, as described, acoustic data is collected with a microphone. The microphone detects an audio sound pressure level (SPL), which is then transformed or converted into a voltage signal. The sound pressure level and voltage are functions of time (spl(t)→v(t)).

In an embodiment, the sampling frequency for the data collection is at least twice the maximum frequency of the physiological phenomenon that is being recorded (in this case, a fluid hitting another fluid, such as urine into a toilet filled with water). This is consistent with the Nyquist-Shannon sampling theorem. The initial frequency, herein f_0, sets the lower limit on the sampling rate. The frequency bandwidth then is defined from f_0 to f_c, where f_c is the maximum frequency. This maximum frequency is defined as twice the maximum frequency that is anticipated to be recorded from the sound of the fluid hitting another fluid (urine hitting the toilet water).

The sampling frequency then defines the sampling rate (delta_t). The delta_t is then used for data collection. In embodiments, a column vector is generated. The column vector is comprised of voltage parameters (representative of the sound frequencies obtained by the microphone) at a specified delta_t.

The number of samples (sample size) is equal to (n−1)*(t/delta_t). An array of flow rates can then be obtained and is herein called Q(t). Q(t) is then correlated with PSD data.

At 706, embodiments calculate the power spectral density of each segment. In an embodiment, the power spectral density is the voltage amplitude of a signal that describes how the variance of the data is distributed over frequency components into which the data may be decomposed. Each sound has varying power between frequency bands. The correlation coefficients are based on these variations in power between flow rate recordings. As such, 704a is configured to identify the unique power distribution of the recorded signal.

At 708, the flow rate is estimated based on the coefficient model and the power spectral density. In an embodiment, as depicted, the flow rate is estimated by matrix multiplication of the coefficient model and the power spectral density. Other algorithms are also considered. In embodiments, correlation coefficients detect power variations specific to abnormal and normal flow rates. A resting estimate is based on a strong similarity between the power spectral density of the recorded signal and that of simulated flow rates.

At 710, additional calculations for other outputs, such as maximum flow rate, minimum flow rate, mean flow rate, and total volume voided can be conducted. For example, embodiments utilize the estimates from 706 to label maximum flow rate and minimum flow rate, calculate mean flow by averaging the estimates, and predict the total volume voided by integrating appropriate data. The resolution of the coefficients allows for embodiments to generate a flow profile that can also be plotted and output in graphical format.

In an embodiment, a time integral of the Q(t) and spl(t) and/or v(t) can be performed in order to determine voided volume. In embodiments, time integrals can be further calculated for minimum and maximum flows.

Figure 8A:
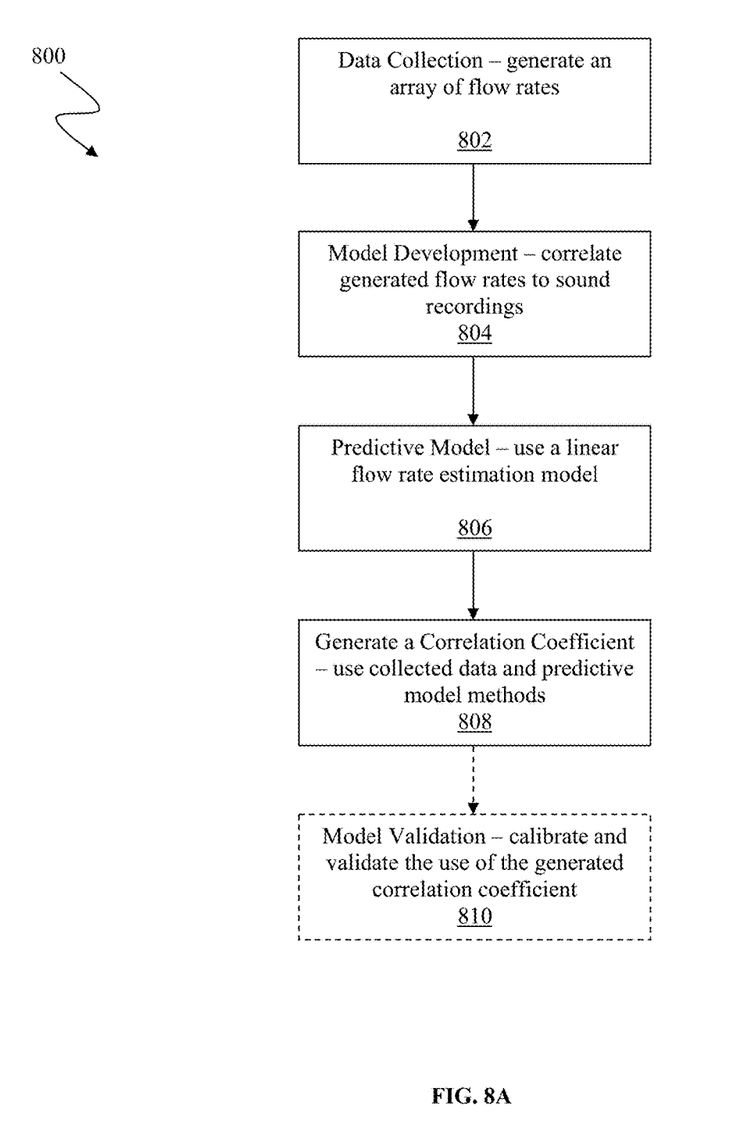
FIG. 8A is a flowchart of a method of coefficient model generation, according to an embodiment.

Referring to FIG. 8A, a flowchart of a method of coefficient model generation 800 is depicted, according to an embodiment. At 802, data collection is conducted.

At 804, model development is conducted. In an embodiment, model development at 804 comprises correlating flow rates to sound recordings.

At 806, a predictive model is made. In an embodiment, a linear flow rate estimation model is utilized for the predictive model. In other embodiments, other estimation or predictive models can be utilized.

At 808, a correlation coefficient is generated. For example, the data collected at 802 can be utilized with the predictive model at 806 to generate a coefficient. In an embodiment, the correlation coefficient comprises a coefficient matrix. In other embodiments, the correlation coefficient comprises single or multiple coefficient values.

Further, method of coefficient model generation 800 can further comprise, optionally at 810, generation of a validation model. For example, at 810, the correlation coefficient can be validated in a particular use. A method of coefficient model validation is depicted in FIG. 8B.

Figure 8B:
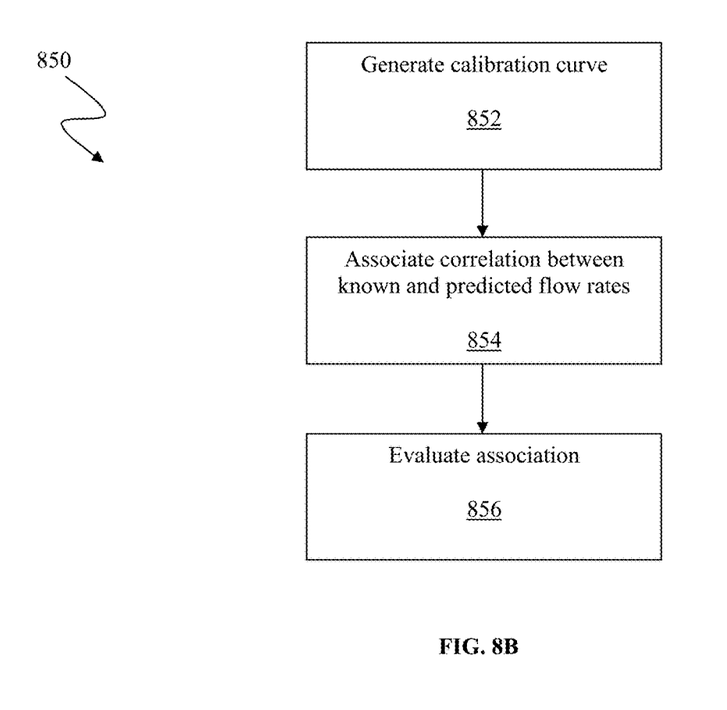
FIG. 8B is a flowchart of a method of coefficient model validation, according to an embodiment.

Referring now to FIG. 8B, a flowchart of a method of coefficient model validation is depicted, according to an embodiment. At 852, a calibration curve is generated. At 854, an association is created between known and predicted flow rates. At 856, the association between known and predicted flow rates can be evaluated. In embodiments, as illustrated in FIG. 8A, correlation coefficient can be generated without generating a calibration curve.

Figure 9:
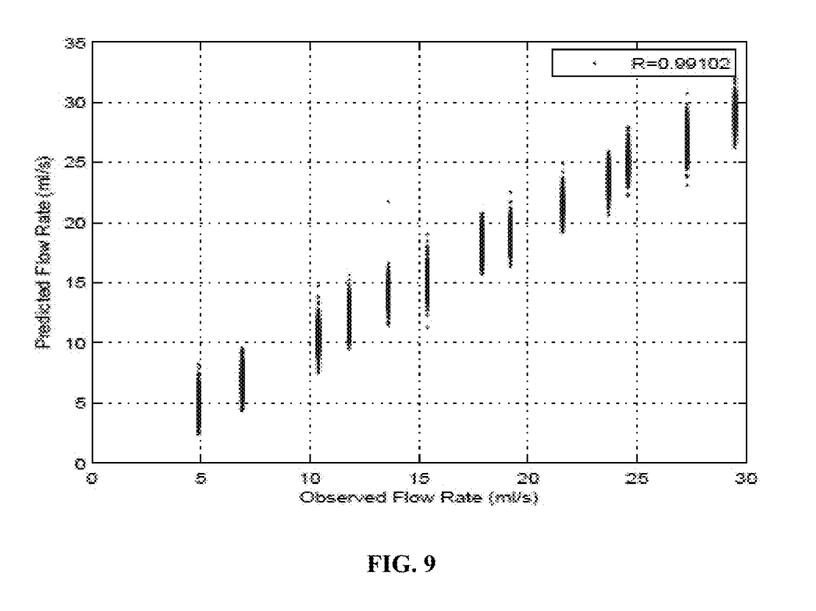
FIG. 9 is a graph of a calibration curve for a flow rate measurement device, according to an embodiment.

For example, referring to FIG. 9, a graph of a calibration curve is depicted. The correlation between the known flow rates and predicted flow rates was found to be strong and linear with an $R^2$ value of 0.991. Each point in FIG. 9 represents the value of the flow rate based on the power signal density of a recording. In this case, the point is generated from 1 second of a test where each test has a duration of 5 seconds held at a fixed flow rate. The embodiment depicted in FIG. 9 is merely one example of producing a calibration curve. For example, it is possible to vary the duration of the test and sampling rate. In embodiments, other graphs reflect one point representing ±1 second of a ±5 second test. In embodiments, the calibration curve produced demonstrates >99% accuracy.

Figure 10:
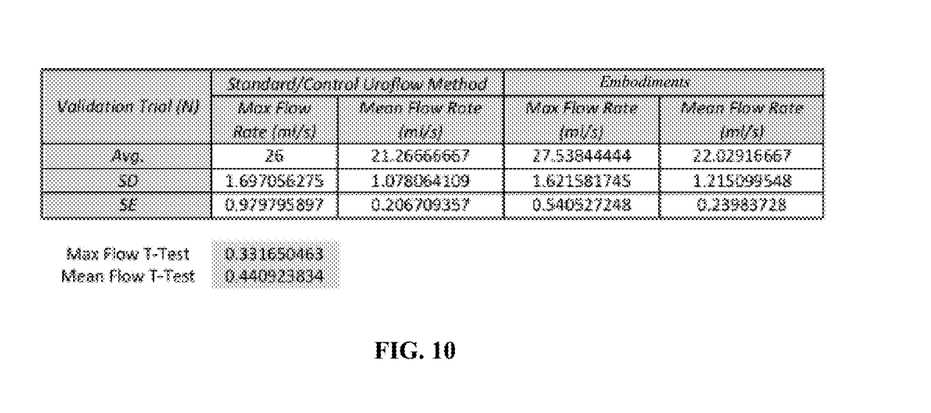
FIG. 10 is a chart of known flow rates and flow rates measured with a flow rate measurement device, according to an embodiment.

Referring to FIG. 10, a chart of known flow rates and flow rates measured with a prototype flow rate measurement device according to embodiments is depicted. In an embodiment of coefficient model validation, tests were performed between the group of known flow rates and the flow rates measured with embodiments of devices described herein. The tests showed no significant difference between data sets, as shown in FIG. 10.

Figure 11:
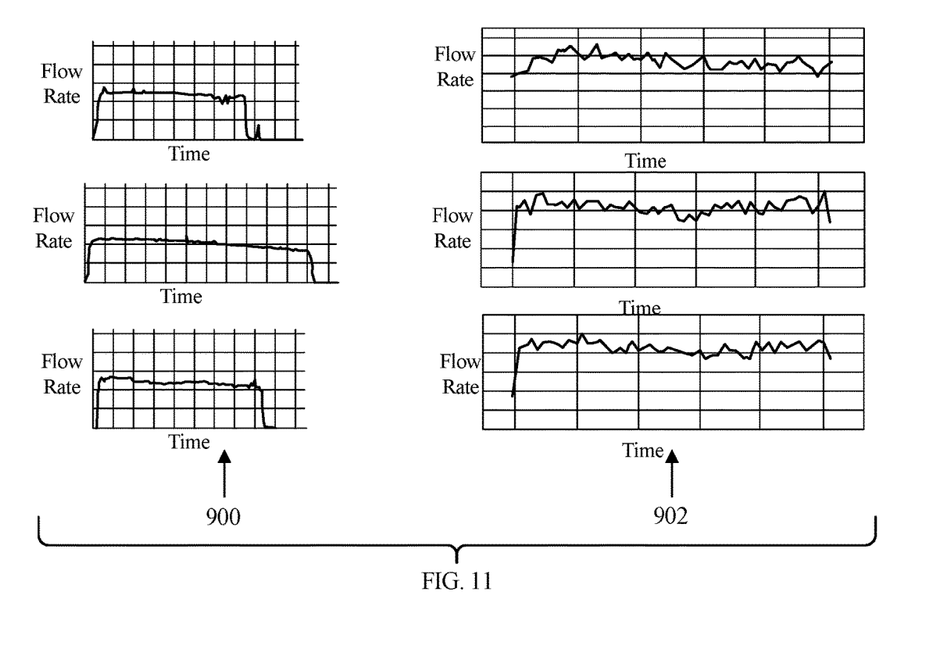
FIG. 11 is graphs of flow rates measured with a traditional uroflowmetry machine and flow rates measured with a flow rate measurement device, according to an embodiment.

Referring to FIG. 11, graphs of flow rates measured with a traditional uroflowmetry machine and flow rates measured with a flow rate measurement device, according to an embodiment. In an embodiment of coefficient model validation, a graphical comparison of validation results of FIG. 8A can be performed. For example, the graphs of 900 were generated with a traditional uroflowmetry machine. The graphs of 902 were generated with embodiments of devices described herein. As illustrated, no visually dissimilar data presentation is depicted.

While embodiments discussed herein relate to human urine flow rate measurement for the detection and to aid in the diagnosis, or provide a diagnosis, of one or more disorders, these and other embodiments can also be used in human feurine flow measurement, and in veterinary applications, for the detection and to aid in the diagnosis of one or more disorders that may affect human populations, or animal populations. Additionally, embodiments are not limited to detecting and aiding in the diagnosis of the example disorders discussed herein, as embodiments can have applicability in detecting and aiding in the diagnosis of others. The examples and discussion related to urine flow rate measurement are not limiting with respect to other applications, uses and embodiments.

In embodiments, a kit can be assembled and/or provided, comprising a flow rate measurement device including a recording unit including at least one sensor and configured to sense and record data related to urine flow rate, and a transmission unit configured to transmit the urine flow rate data; a calibration device configured to calibrate the data related to urine flow rate sensed by the flow rate measurement device; and instructions for using at least one of the flow rate measurement device or the calibration device. The kit can further comprise a mounting accessory adapted to operably couple the flow rate measurement device to a toilet. The kit can also, instead or in addition, further comprise a remote device configured to receive the urine flow rate data and present a diagnosis of lower urinary tract symptoms. The kit can also, instead or in addition, further comprise software implemented by a processor and configured to provide the recording unit and the transmission unit.

In embodiments, devices disclosed herein can be, contain or comprise one or more processors, microprocessors and/or other computer or computing devices. These devices discussed herein can be any programmable device that accepts digital data as input, is configured to process the input according to instructions or algorithms, and provides results as outputs. In an embodiment, processors and other such devices discussed herein can be, comprise, contain or be coupled to a central processing unit (CPU) configured to carry out the instructions of a computer program. Processors and other such devices discussed herein are therefore configured to perform basic arithmetical, logical, and input/output operations.

Processors and other devices discussed herein can include memory. Memory can comprise volatile or non-volatile memory as required by the coupled computing device or processor to not only provide space to execute the instructions or algorithms, but to provide the space to store the instructions themselves. In embodiments, volatile memory can include random access memory (RAM), dynamic random access memory (DRAM), or static random access memory (SRAM), for example. In embodiments, non-volatile memory can include read-only memory, flash memory, ferroelectric RAM, hard disk, floppy disk, magnetic tape, or optical disc storage, for example. The foregoing lists in no way limit the type of memory that can be used, as these embodiments are given only by way of example and are not intended to limit the scope of the invention.

In embodiments, the system, devices or components thereof can comprise or include various engines, each of which is constructed, programmed, configured, or otherwise adapted, to autonomously carry out a function or set of functions. The term "engine" as used herein is defined as a real-world device, component, or arrangement of components implemented using hardware, such as by an application specific integrated circuit (ASIC) or field-programmable gate array (FPGA), for example, or as a combination of hardware and software, such as by a microprocessor system and a set of program instructions that adapt the engine to implement the particular functionality, which (while being executed) transform the microprocessor system into a special-purpose device. An engine can also be implemented as a combination of the two, with certain functions facilitated by hardware alone, and other functions facilitated by a combination of hardware and software. In certain implementations, at least a portion, and in some cases, all, of an engine can be executed on the processor(s) of one or more computing platforms that are made up of hardware (e.g., one or more processors, data storage devices such as memory or drive storage, input/output facilities such as network interface devices, video devices, keyboard, mouse or touchscreen devices, etc.) that execute an operating system, system programs, and application programs, while also implementing the engine using multitasking, multithreading, distributed (e.g., cluster, peer-peer, cloud, etc.) processing where appropriate, or other such techniques. Accordingly, each engine can be realized in a variety of physically realizable configurations, and should generally not be limited to any particular implementation exemplified herein, unless such limitations are expressly called out. In addition, an engine can itself be composed of more than one sub-engines, each of which can be regarded as an engine in its own right. Moreover, in the embodiments described herein, each of the various engines corresponds to a defined autonomous functionality; however, it should be understood that in other contemplated embodiments, each functionality can be distributed to more than one engine. Likewise, in other contemplated embodiments, multiple defined functionalities may be implemented by a single engine that performs those multiple functions, possibly alongside other functions, or distributed differently among a set of engines than specifically illustrated in the examples herein.

Various embodiments of systems, devices, and methods have been described herein. These embodiments are given only by way of example and are not intended to limit the scope of the invention. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the invention.

Persons of ordinary skill in the relevant arts will recognize that the invention may comprise fewer features than illustrated in any individual embodiment described above. The embodiments described herein are not meant to be an exhaustive presentation of the ways in which the various features of the invention may be combined. Accordingly, the embodiments are not mutually exclusive combinations of features; rather, the invention may comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims for the present invention, it is expressly intended that the provisions of Section 112, sixth paragraph of 35 U.S.C. are not to be invoked unless the specific terms "means for" or "step for" are recited in a claim.

The invention claimed is:

1. A urine flow rate measurement device comprising:
   a recording unit arranged at an outpatient location, the recording unit including at least one sensor and configured to sense and record data related to urine flow rate at the outpatient location;
   a memory having a stored model and coupled to the recording unit;
   an analysis unit configured to produce analyzed urine flow rate data from the data related to urine flow rate at the outpatient location, wherein:
      the analysis unit is coupled to the recording unit to receive the recorded urine flow rate data and generate a corresponding data collection, and
      the analysis unit is coupled to the memory such that the analysis unit can compare the stored model and the data collection to produce analyzed urine flow rate data; and
   a transmission unit comprising a wired or wireless hardware configured to transmit the analyzed urine flow rate data to an outside device at a healthcare provider, wherein the outside device is remote from the outpatient location.

2. The urine flow rate measurement device of claim 1, wherein the at least one sensor is an acoustic sensor, and the data related to urine flow rate is acoustic wave data.

3. The urine flow rate measurement device of claim 1, wherein the at least one sensor is a camera, and the data related to urine flow rate is physical wave data.

4. The urine flow rate measurement device of claim 1, wherein the transmission unit comprises an antenna configured to wirelessly transmit the analyzed urine flow rate data.

5. The urine flow rate measurement device of claim 1, wherein the analysis unit is configured to analyze the recorded urine flow rate data by at least a coefficient model and a power spectral density of the recorded urine flow rate data.

6. The urine flow rate measurement device of claim 1, wherein the device is configured to be operably coupled proximate a toilet.

7. A system for determining lower urinary tract symptoms, the system comprising:
   a flow rate measurement device including:
      a recording unit arranged at an outpatient location, the recording unit including at least one sensor and configured to sense and record data related to urine flow rate at the outpatient location, and
      a transmission unit configured to transmit the urine flow rate data;
   a memory having a stored model and coupled to the recording unit;
   a remote device arranged at the outpatient location, the remote device configured to receive the urine flow rate data and present a determination of lower urinary tract symptoms based on a comparison of the urine flow rate data and the stored model, the remote device comprising a wired or wireless hardware configured to transmit the analyzed urine flow rate data to an outside device at a healthcare provider, wherein the outside device is remote from the outpatient location.

8. The system of claim 7, wherein the remote device is further configured to analyze the received urine flow rate data.

9. The system of claim 8, wherein the remote device is configured to analyze the recorded urine flow rate data by at least one of a coefficient model and a power spectral density of the recorded urine flow rate data.

10. The system of claim 7, wherein the flow rate measurement device further comprises an analysis unit configured to analyze the recorded urine flow rate data, wherein the recorded urine flow rate is analyzed prior to transmission to the remote device.

11. The system of claim 10, wherein the analysis unit is configured to analyze the recorded urine flow rate data by at least one of a coefficient model or a power spectral density of the recorded urine flow rate data.

12. The system of claim 7, further comprising a calibration device configured to calibrate the data related to urine flow rate sensed by the flow rate measurement device.

13. The system of claim 7, wherein the remote device is at least one of a cell phone, a tablet, a laptop computer, a desktop computer, a PDA, or a watch.

14. The system of claim 7, further comprising a wireless communication channel that communicatively couples the flow rate measurement device and the remote device.

15. The system of claim 7, wherein the at least one sensor is an acoustic sensor, and the data related to urine flow rate is acoustic wave data.

16. The system of claim 7, wherein the at least one sensor is a camera, and the data related to urine flow rate is physical wave data.

17. A method of determining lower urinary tract symptoms, the method comprising:
   placing a flow rate measurement device proximate a urine receptacle at an outpatient location;
   recording, using the flow rate measurement device at the outpatient location, data related to urine flow rate;
   storing the recorded urine flow rate data as a data collection;
   analyzing the recorded urine flow rate data by comparing a stored model and the data collection to produce analyzed urine flow rate data;
   transferring the analyzed urine flow rate data to an outside device at a healthcare provider remote from the outpatient location; and
   presenting the analyzed urine flow rate data.

18. The method of claim 17, further comprising generating a graph of the analyzed urine flow rate data.

19. The method of determining lower urinary tract symptoms of claim 17, wherein analyzing the recorded urine flow rate data comprises at least one of generating a coefficient model, or utilizing a power spectral density of the recorded urine flow rate data.

* * * * *